US012153635B2

(12) United States Patent
Elenchin et al.

(10) Patent No.: US 12,153,635 B2
(45) Date of Patent: Nov. 26, 2024

(54) GENERATING CDA DOCUMENTS UTILIZING FHIR RESOURCES

(71) Applicant: CERNER INNOVATION, INC., Kansas City, KS (US)

(72) Inventors: Alison Elizabeth Elenchin, Pottsville, PA (US); Douglas Charles Pratt, Downingtown, PA (US)

(73) Assignee: Cerner Innovation, Inc., Kansas City, MO (US)

(*) Notice: Subject to any disclaimer, the term of this patent is extended or adjusted under 35 U.S.C. 154(b) by 565 days.

(21) Appl. No.: 16/701,940

(22) Filed: Dec. 3, 2019

(65) Prior Publication Data

US 2021/0165836 A1 Jun. 3, 2021

(51) Int. Cl.
| | |
|---|---|
| G06F 16/93 | (2019.01) |
| G06F 9/50 | (2006.01) |
| G06F 9/54 | (2006.01) |
| G06F 16/2455 | (2019.01) |
| G06F 16/25 | (2019.01) |
| G16H 10/60 | (2018.01) |

(52) U.S. Cl.
CPC ........... *G06F 16/93* (2019.01); *G06F 9/5005* (2013.01); *G06F 9/54* (2013.01); *G06F 16/24565* (2019.01); *G06F 16/252* (2019.01); *G16H 10/60* (2018.01)

(58) Field of Classification Search
CPC ......... H04L 67/12; H04L 67/02; G06F 16/25; G06F 16/2465; G06F 16/93; G06F 21/6245; G06F 21/6254
See application file for complete search history.

(56) References Cited

U.S. PATENT DOCUMENTS

| | | | |
|---|---|---|---|
| 7,392,237 B2 | 6/2008 | Pratt | |
| 8,117,042 B2 | 2/2012 | Braz et al. | |
| 8,732,209 B2 | 5/2014 | Griffin et al. | |
| 8,856,156 B1 | 10/2014 | Mcnair et al. | |
| 10,706,959 B1* | 7/2020 | Tevis | G06F 16/137 |
| 2011/0295873 A1* | 12/2011 | Potter | G16H 40/20 |
| | | | 707/769 |
| 2012/0060216 A1* | 3/2012 | Chaudhri | G06Q 10/10 |
| | | | 726/21 |

(Continued)

FOREIGN PATENT DOCUMENTS

WO WO-2012031052 A2 * 3/2012 ............. G06Q 10/10

OTHER PUBLICATIONS

H. Kondylakis, Y. Petrakis, S. Leivadaros, G. Iatraki and D. Katehakis, "Using XDS and FHIR to Support Mobile Access to EHR Information Through Personal Health Apps," 2019 IEEE 32nd International Symposium on Computer-Based Medical Systems (CBMS), 2019, pp. 241-244, doi: 10.1109/CBMS.2019.00058. (Year: 2019).*

(Continued)

*Primary Examiner* — Tom Y Chang
(74) *Attorney, Agent, or Firm* — Invoke

(57) ABSTRACT

Embodiments herein disclose systems, methods, and computer-readable media for generating CDA (Clinical Document Architecture) documents from Fast Healthcare Interoperability Resources (FHIR) APIs utilizing a unified, flexible, cloud-based service that can be leveraged across disparate solutions and/or systems.

26 Claims, 4 Drawing Sheets

(56) References Cited

U.S. PATENT DOCUMENTS

| | | | | |
|---|---|---|---|---|
| 2015/0310176 | A1* | 10/2015 | Chen | H04L 51/214 |
| | | | | 705/2 |
| 2015/0370969 | A1* | 12/2015 | Tambasco, Jr. | G16H 10/60 |
| | | | | 705/3 |
| 2017/0103163 | A1* | 4/2017 | Emanuel | G16Z 99/00 |
| 2017/0161439 | A1* | 6/2017 | Raduchel | H04W 12/06 |
| 2017/0287093 | A1* | 10/2017 | Tochilnik | G06F 16/113 |
| 2018/0293351 | A1* | 10/2018 | Simons | G16H 15/00 |
| 2019/0103173 | A1* | 4/2019 | Power | H04L 67/12 |
| 2020/0160955 | A1* | 5/2020 | Hansen | G06Q 40/08 |

OTHER PUBLICATIONS

Y. Petrakis, A. Kouroubali and D. Katehakis, "A Mobile App Architecture for Accessing EMRs Using XDS and FHIR," 2019 IEEE 19th International Conference on Bioinformatics and Bioengineering (BIBE), 2019, pp. 278-283, doi: 10.1109/BIBE.2019.00057. (Year: 2019).*

M. Mercorella, M. Ciampi, M. Esposito, A. Esposito and G. De Pietro, "An Architectural Model for Extracting FHIR Resources from CDA Documents," 2016 12th International Conference on Signal-Image Technology & Internet-Based Systems (SITIS), 2016, pp. 597-603, doi: 10.1109/SITIS.2016.99. (Year: 2016).*

Demski, H., Garde, S. & Hildebrand, C. Open data models for smart health interconnected applications: the example of openEHR. BMC Med Inform Decis Mak 16, 137 (2016). https://doi.org/10.1186/s12911-016-0376-2 (Year: 2016).*

Panagiotis Plastiras, Dympna O'Sullivan, Exchanging personal health data with electronic health records: . . . living, International Journal of Medical Informatics, vol. 120,2018, pp. 116-125,https://doi.org/10.10 (Year: 2018).*

Matt Szczepankiewicz C-CDA Examplees Nov. 12, 2014 22pages https://github.com/HL7/C-CDA-Examples/blob/master/Documents/CCD/CCD%202/CCD.XML retrieved from internet Jul. 28, 2023 (Year: 2014).*

FHIR HL7 Restful API release 2.1.0 pp. 1-21 https://hl7.org/fhir/DSTU2/http.html retrieved from internet Mar. 31, 2024 (Year: 2015).*

* cited by examiner

GENERATING CDA DOCUMENTS UTILIZING FHIR RESOURCES

BACKGROUND

CDA (Clinical Document Architecture) is a standardized structured data format used to create documents (e.g., CDA documents) and template methodologies for documents. The primary function of CDA is to standardize the content and structure for clinical care summaries which, in turn, provides a standardized document for data exchange. Exemplary exchanges include, but are not limited to, provider to patient, primary care provided (PCP) to specialist provider, inpatient environment to an outpatient environment, electronic health record (EHR) system to EHR system transitions, and the like.

Current approaches to create CDA documents are achieved by reading a system's (e.g., healthcare system) own database directly. When a CDA document is created, the code used to create it is bound to the structure of the database. Thus, if there is a change in the database, the code has to be updated as well. This requires an enormous amount of resources and knowledge of coding requirements. Additionally, this approach is intricately tied to the layout of the database. Thus, the accessing party needs to have coding that knows how to read the specific database and tables therein, and can generate a CDA document.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims as supported by the Specification, including the Detailed Description and Drawings.

In brief and at a high level, embodiments of the present invention provide systems, methods, and computer-readable media for generating CDA (Consolidated Clinical Document Architecture) documents from Fast Healthcare Interoperability Resources (FHIR) APIs utilizing a unified, flexible, cloud-based service that can be leveraged across disparate solutions and/or systems. Embodiments provide an application and/or cloud-based service that coordinates with various components of a system to create items and communicate said items across various disparate systems.

One embodiment provides one or more non-transitory computer-readable media having computer-executable instructions embodied thereon that, when executed by a processor of a computer device, perform a method. The method comprises identifying a triggering event, wherein the triggering event initiates creation of an item associated with at least one script, wherein the at least one script includes instructions indicating data to include in the item, and wherein the script includes at least one mapping of a Fast Healthcare Interoperability Resources (FHIR) resource to a resource of at least one standard; querying a first source system for the data indicated in the at least one script to be included in the item; and creating the item utilizing the at least one mapping of the FHIR resource to the resource of the at least one standard.

Another embodiment provides one or more non-transitory computer-readable media having computer-executable instructions embodied thereon that, when executed by a processor of a computer device, perform a method. In accordance with the media, the method comprises identifying a triggering event, wherein the triggering event initiates creation of an item associated with at least one script, wherein the at least one script includes instructions indicating data to include in the item, and wherein the script includes at least one mapping of a Fast Healthcare Interoperability Resources (FHIR) resource to a resource of at least one standard; querying a first source system for the data indicated in the at least one script to be included in the item; creating the item utilizing the at least one mapping of the FHIR resource to the resource of the at least one standard; designating a first destination for the item, wherein the first destination is disparate from the first source system; and communicating the item to the first destination utilizing a messaging protocol.

Yet another embodiment provides a system for clinical interoperability of disparate systems. The system comprises one or more processors configured to identify a triggering event, wherein the triggering event initiates creation of an item associated with at least one script, wherein the at least one script includes instructions indicating data to include in the item, and wherein the script includes at least one mapping of a Fast Healthcare Interoperability Resources (FHIR) resource to a resource of at least one standard; query a first source system for the data indicated in the at least one script to be included in the item; create the item utilizing the at least one mapping of the FHIR resource to the resource of the at least one standard; designate a first destination for the item, wherein the first destination is disparate from the first source system; and communicate the item to the first destination utilizing a messaging protocol.

BRIEF DESCRIPTION OF THE DRAWINGS

Embodiments are described in detail below with reference to the attached drawings figures, wherein.

DETAILED DESCRIPTION

Figure 1:
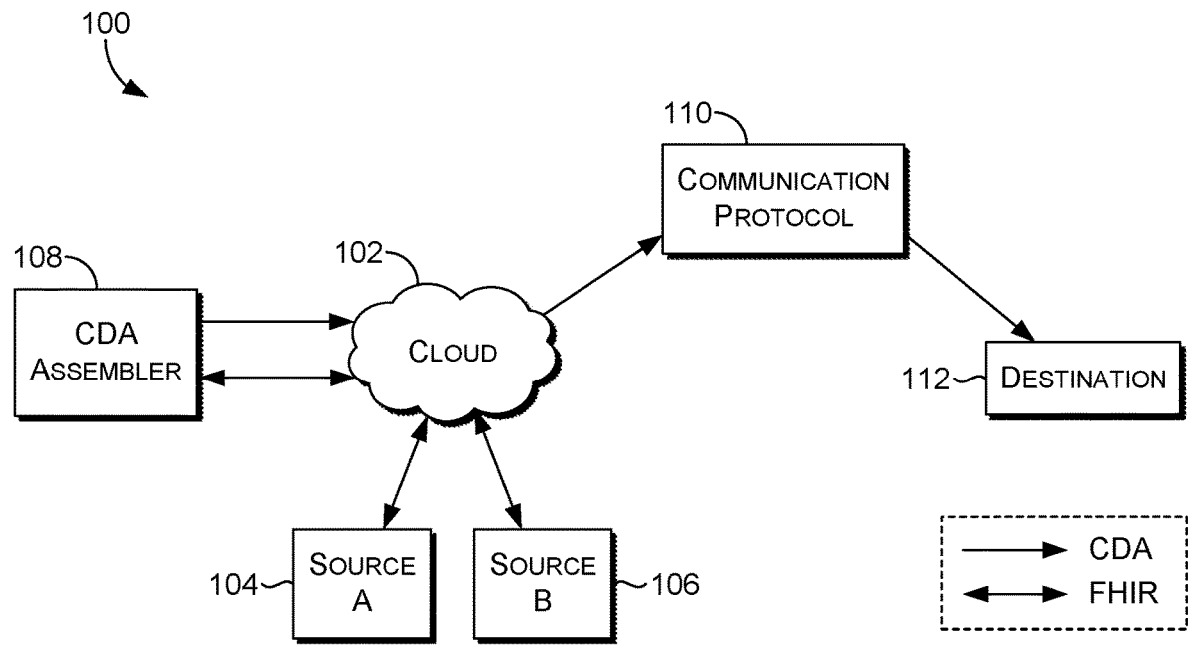
FIG. 1 depicts a block diagram of an exemplary system architecture in accordance with an embodiment of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the disclosure may be embodied as, among other things: a method, system, or set of instructions embodied on one or more computer-readable media. Accordingly, the embodiments may take the form of a hardware embodiment, a software embodiment, or an embodiment combining software and hardware. In one embodiment, the invention takes the form of a computer-program product that includes computer-useable instructions embodied on one or more computer-readable media, as discussed further herein.

Embodiments of the present invention provide systems, methods, and computer-readable media for generating CDA (Consolidated Clinical Document Architecture) documents from Fast Healthcare Interoperability Resources (FHIR) APIs utilizing a unified, flexible, cloud-based service that can be leveraged across disparate solutions and/or systems. Embodiments provide an application and/or cloud-based service that coordinates with various components of a system to create items and communicate said items across various disparate systems.

At a high level, embodiments of the present invention provide a customized and complex software product that specifically addresses a need to achieve interoperability across disparate sources with respect to generation of items such as CDA documents. The software product can communicate with one or more disparate sources to, among other things, access data from an EHR system, store health data in an EHR system, generate one or more items (e.g., a CDA document), and the like. The software product can provide the integration with an EHR system while preserving privacy of an individual and the data associated therewith accessed from the EHR system.

Certified EHR systems are required, by federal regulations, to be API-enabled. This allows for third parties to create applications, programs, etc., to access data within the EHR system. Each system is typically embedded with proprietary code to create specific items, such as CDA documents. The systems utilize the proprietary code to read their own databases directly to generate requested items. This is problematic for a variety of reasons. Initially, upkeep of the proprietary code is a highly technical task that consumes a lot of manpower and requires a highly skilled computer programmer to be able to modify the code when needed. Those modifications, unfortunately, are often since each time a change is made to the database a change is also required in the code. The code is very tied to the database. Second, there is no way for third parties that need to access data to create items to know (nor should they know) the proprietary code or the structure of the database necessary to generate the items.

The present solution seeks to solve this technical problem by relying on FHIR APIs to assemble the data needed and create requested items across disparate systems. FHIR can provide a layer of insulation from the particulars of a database. It allows the present solution to operate as a cloud-based solution and service multiple systems. The use of FHIR provides a means to expose the underlying data of a database via a FHIR API to third parties without knowledge of the database layout. In particular, the use of FHIR APIs in the present solution creates CDA xml documents from FHIR API calls using a CDA assembler, as described in detail herein, to generate the items/documents using FHIR resources. This eliminates the need for the hard-coding to the system database specification to create items from the content therein. This also eliminates the dual development associated with updates (i.e., an update is made to the CDA document so the API has to be updated and, with current solutions, the proprietary code; this update to the proprietary code is eliminated in the proposed solution).

Additionally, this allows for CDA assemblers to be associated with multiple EHR systems, rather than a single EHR.

Referring to the drawings in general, and initially to FIG. 1, a block diagram illustrating an exemplary system 100 architecture in which some embodiments of the present disclosure may be employed. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory.

It should be understood that the system 100 shown in FIG. 1 is an example of one suitable computing system architecture. Each of the components of FIG. 1 may be implemented via any type of computing device. The components can communicate with each other via a network including, without limitation, one or more local area networks (LANs) and/or wide area networks (WANs). Such networking environments are commonplace in offices, enterprise-wide computer networks, intranets, and the Internet. It should be understood that any number of components shown in FIG. 1 may be employed within the system 100 within the scope of the present invention. Each may be implemented via a single device or multiple devices cooperating in a distributed environment. Additionally, other components not shown may also be included within the environment.

Among other components not shown, the system 100 includes a variety of source systems, such as Source A 104 and Source B 106 (the sources can be an EHR server), a CDA assembler, a communication protocol 110, and a destination 112, any of which can interact with any other component of the system 100 and each of which are communicatively coupled with each other. These components may communicate with each other via networking means (e.g., network 102) which may include, without limitation, one or more local area networks LANs and/or wide area networks (WANs). In exemplary implementations, such networks comprise the Internet and/or cellular networks, amongst any of a variety of possible public and/or private networks.

A source device (not shown) can comprise any type of computing device capable of use by a user. By way of example and not limitation, a source device can be embodied as a personal computer (PC), a laptop computer, a mobile device, a smartphone, a tablet computer, a smart watch, a wearable computer, a fitness tracker, a personal digital assistant (PDA) device, a global positioning system (GPS) device, a video player, a handheld communications device, an embedded system controller, a camera, a remote control, a wearable electronic device with a camera (e.g., smart glasses, gesture-based wearable computers, etc.) a consumer electronic device, a workstation, or any combination of these delineated devices, a combination of these devices, or any other suitable computer device. The source device, as applied herein, can be utilized to access, for instance, the cloud-based solution to request creation of the item.

The sources, Source A 104 and Source B 106, can be an EHR server or any system that maintains, and provides access to, one or more EHR database(s) containing records of treatment events, medication history, diagnoses, problems, allergies, demographic attributes, laboratory tests, time and date data, and any other health-related data, or any combination thereof for a plurality of patients. Additionally, the sources 104 and 106 can include clinical notes, appointment notes, records of issued prescriptions, diagnoses, care plans, bloodwork, urinalysis, treatment data, emergency contact information, and the like, for each patient of a healthcare facility or a plurality of healthcare facilities. Further, sources 104 and 106 can include images, representations, or clinical documentation of physical health data (e.g., X-rays, CT scans, ultrasound images, etc.). Additionally, in some embodiments, sources 104 and 106 can maintain one or more pharmaceutical formularies that identify prescriptions prescribed by, or available for prescription by, care providers. While described concurrently, Source A 104 and Source B 106 are meant to depict separate, disparate systems. For example, Source A 104 may be associated with a healthcare facility 1 (e.g., a patient's PCP clinical office) while Source B 106 may be associated with healthcare facility 2 (e.g., a hospital emergency department).

Communication protocol 110 provides a secure means to communicate content from the CDA Assembler 108 to one or more disparate sources, such as destination 112. The destination, shown herein as a separate destination 112, can be a source system. The destination 112 is disparate from the source system queried for the data to create a requested item/document. Any protocol may be used by communication protocol 110 that provides secure communication means across a network to a plurality of disparate sources.

CDA Assembler 108 can facilitate interoperability between, for instance, Source A 104 and Source B 106, with respect to generation of documents and transmission thereof. CDA Assembler 108 can facilitate communication between a plurality of disparate sources that are each FHIR-enabled and integrated with the cloud (e.g., network 102). CDA Assembler 108 can include an API library that includes specifications for routines, data structures, object classes, and variables that support the interaction of the CDA Assembler 108 architecture and the software framework of one or more disparate sources (e.g., Source A 104, Source B 106, etc.). These APIs can include configuration specifications for the system 100 such that the components therein may communicate with each other, as described herein.

The APIs allow third parties (e.g., patients, sources disparate from the source housing the data, etc.) to query a source database, via the API, for CDA documents or information contained therein (e.g., medication list, allergy list, problem list, diagnostic test results, etc.) or other specified information. As previously mentioned, FHIR is the predominant API standard and provides a layer of insulation between the CDA assembler 108 and a database of the source system (e.g., Source A 104) such that the underlying data of the database is exposed.

Figure 2:
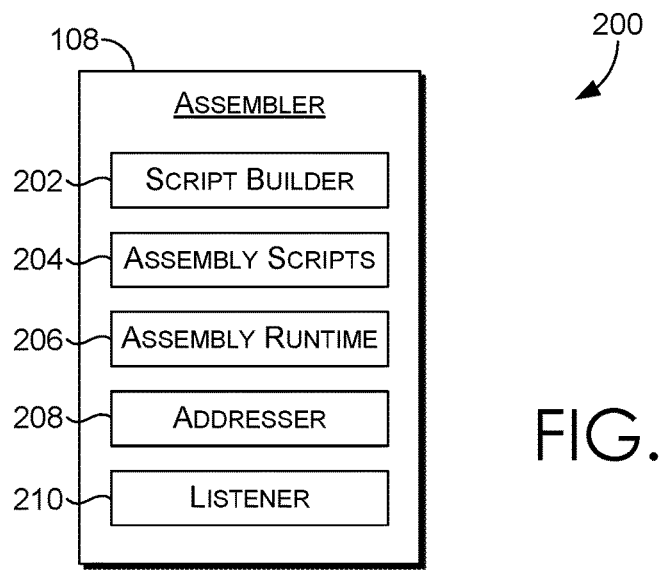
FIG. 2 depicts a block diagram of an exemplary assembler component in accordance with an embodiment of the present invention.

The CDA Assembler 108 is independent of an EHR system or any sources described herein. The CDA Assembler 108 connects to FHIR resources and, as shown in FIG. 2, includes a script builder 202, assembly scripts 204, an assembly runtime 206, an addresser 208, and a listener 210.

Script builder 202 can be a tool within the CDA assembler 108 that allows a user (e.g., hospital, medical system, etc.) to build a script for use by the CDA assembler 108. A script, as used herein, is a set of at least one instruction indicating specific data to include in a requested item. Scripts, therefore, can include at least one mapping of a FHIR resource to a resource of at least one standard (outside of FHIR). For example, the script can include a mapping from FHIR to CDA. A user can, with the use of the script builder 202, generate custom scripts for their system. A user can indicate a mapping of a FHIR API component to a CDA component to generate a CDA document from a FHIR API. The script, in short, includes instructions on what data to include or exclude in a requested item, such as a CDA document. An exemplary script mapping is provided below:

Map [FHIR API RESOURCE] to [CDA RESOURCE]
Output SOEN CDA xml document

An additional exemplary script mapping is provided below:

Map [FHIR.Allergy.Intolerance.code] to
[/ClinicalDocument/ . . . /participantRole/playingEntity/code/translation/@code.[CSM]

The scripts can be compiled in the assembly scripts 204. Assembly scripts 204 can include one or more custom scripts that, as described above, are generated by a user. Users can create as many scripts as desired for any items necessary. Assembly scripts 204 can also include one or more template scripts that can be provided in the tool. The one or more template scripts can be customized by the user and saved as a custom script. The assembly scripts 204 may be unique to a system or can be a public repository for sharing of scripts.

The assembly runtime 206 can comprise code that interprets the scripts produced and executes them. At a prescribed time, the assembly runtime 206 can create the item. The assembly runtime 206 can create the item(s) from FHIR resources and can create the item(s) on-demand. In other words, a user can request that an item be created and, in near real-time, the assembly runtime 206 can begin interpreting scripts and executing said scripts to create the items. The prescribed time, as referenced above, can be a predetermined time (e.g., 24 hours post-discharge, after a scheduled job, and the like) or an on-demand request (e.g., user requests that the CDA assembler 108 generate an item). The assembly runtime 206 can identify that it is the prescribed time to generate an item upon being notified of a triggering event by the listener 210. Listener 210 can identify when to assemble, address, and send CDA documents based on identification of a triggering event. A triggering event, as used herein, refers generally to an action or occurrence that initiates generation of an item by the assembly runtime 206. Background triggers can be predetermined times and happen without any user interaction (e.g., 24 hours post-discharge, etc.). User-initiated triggers can be triggers that are on-demand from a user. User-initiated triggers require action from a user to initiate the request.

Addresser 208 can identify a destination (e.g., health information exchanges, a specialist clinician, etc.) associated with the item. The addresser 208 can then work with the communication protocol 110 to transmit the item from the originating source (e.g., Source A 104) to the destination 112.

Having briefly described the components of system 100 and the assembler 108 illustrated in block diagram 200, exemplary component interactions of the components of FIGS. 1 and 2 are now described. In application, a user can initiate a request for an item to be generated. The user, for example, can be a clinician (e.g., PCP) and can be requesting for an item to be generating during an encounter with a patient. The clinician may be, for example, requesting that a CDA document be generated and sent to a cardiologist specialist to whom the clinician is referring the patient. The user/clinician can initiate the request via the script builder tool, which may be provided in a script builder user interface provided to users for the generation of item requests. The user can graphically design the instructions at that point (i.e., define a customized script) or can access a template script. In this example, the clinician may want to access a template script for generation of a CDA document or create a custom script.

The scripts map FHIR resources to resources of another standard, such as CDA. FHIR resources can be individual packets of information that include metadata, text, data elements, and the like, or can be bundled into collections of resources that create clinical documents, such as CDA documents. Exemplary FHIR resources include DocumentReference resource (describes a document that is located elsewhere), Patient resource, Provider resource, Organization resource, and the like. To utilize the CDA assembler 108, the source of the data should be FHIR-enabled.

Once created, the listener 210 can identify an on-demand user initiated trigger requesting an item and notify the assembly runtime 204. The assembly runtime 204 can then interpret the instructions of the script and execute the script. Execution of the script, as used herein, refers generally to accessing data indicated in the script and compiled said data to create the requested item. Execution is achieved by querying the originating source for the requested data via a FHIR API call. The requested items are then received by the assembly runtime 204 and compiled in the requested document.

The addresser 208 can address the item, according to the instructions in the script, and communicate with the communication protocol 110 for communication of the item to one or more destinations disparate from the originating source (such as destination 112).

As is shown in FIG. 1, FHIR APIs are utilized between the CDA assembler 108, the cloud 102, Source A 104, Source B 106, and any other originating sources (not shown) while the output to the communication protocol 110 is in CDA format.

The application described herein provides interoperability between numerous systems to exchange private information and provide the information in necessary situations while still preserving the sensitive nature of the information.

Figure 3:
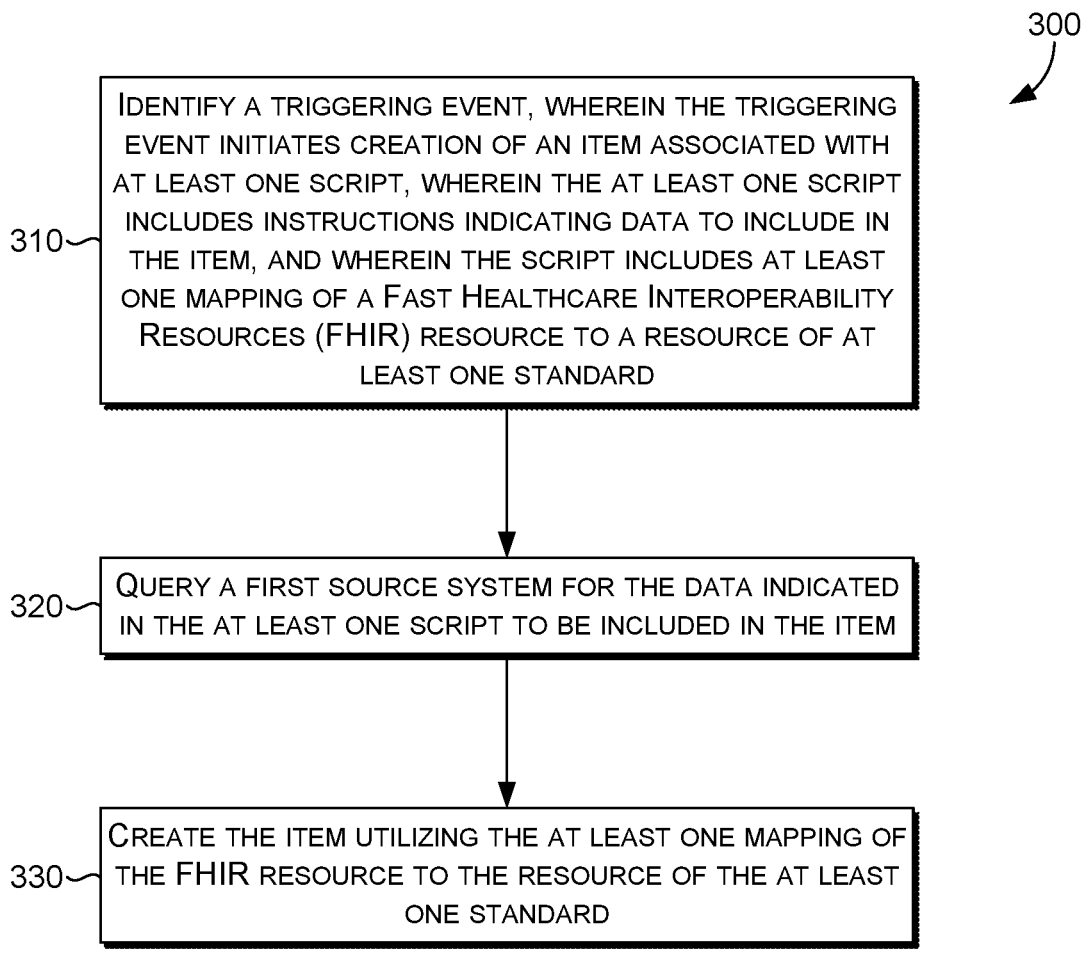
FIG. 3 is a flow diagram of an exemplary method in accordance with an embodiment of the present invention.

Turning now to FIG. 3, a flow diagram is provided showing a method 300 in accordance with some embodiments of the present invention. Initially, at block 310, a triggering event is identified, wherein the triggering event initiates creation of an item associated with at least one script, wherein the at least one script includes instructions indicating data to include in the item, and wherein the script includes at least one mapping of a Fast Healthcare Interoperability Resources (FHIR) resource to a resource of at least one standard. At block 320, a first source system is queried for the data indicated in the at least one script to be included in the item. At block 330, the item is created utilizing the at least one mapping of the FHIR resource to the resource of the at least one standard.

Figure 4:
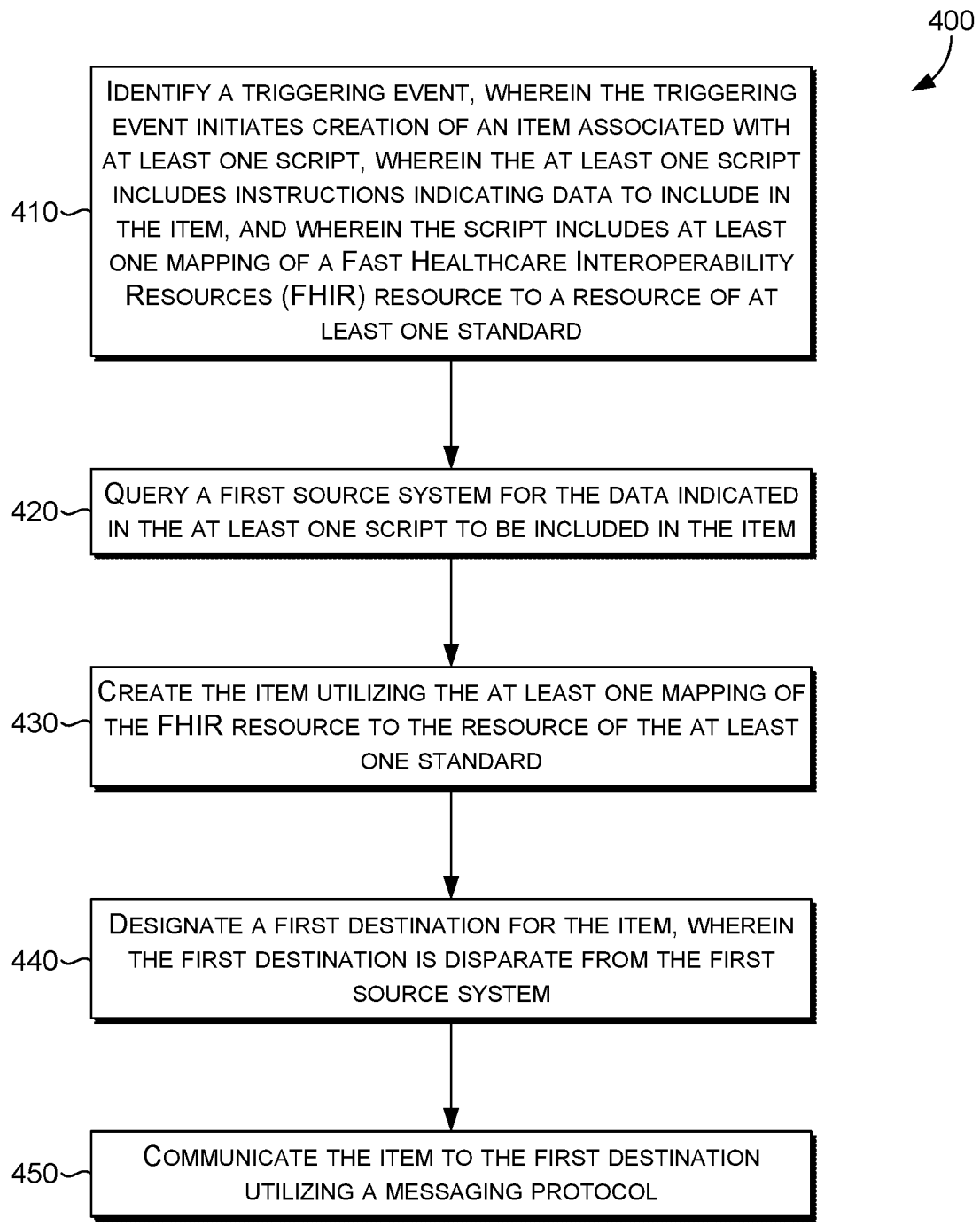
FIG. 4 is a flow diagram of an exemplary method in accordance with an embodiment of the present invention.

Turning now to FIG. 4, a flow diagram is provided showing a method 400 in accordance with some embodiments of the present invention. Initially, at block 410, a triggering event is identified, wherein the triggering event initiates creation of an item associated with at least one script, wherein the at least one script includes instructions indicating data to include in the item, and wherein the script includes at least one mapping of a Fast Healthcare Interoperability Resources (FHIR) resource to a resource of at least one standard. At block 420, a first source system is queried for the data indicated in the at least one script to be included in the item. At block 430, the item is created utilizing the at least one mapping of the FHIR resource to the resource of the at least one standard. At block 440, a first destination is designated for the item, wherein the first destination is disparate from the first source system. Finally, at block 450, the item is communicated to the first destination utilizing a messaging protocol.

Figure 5:
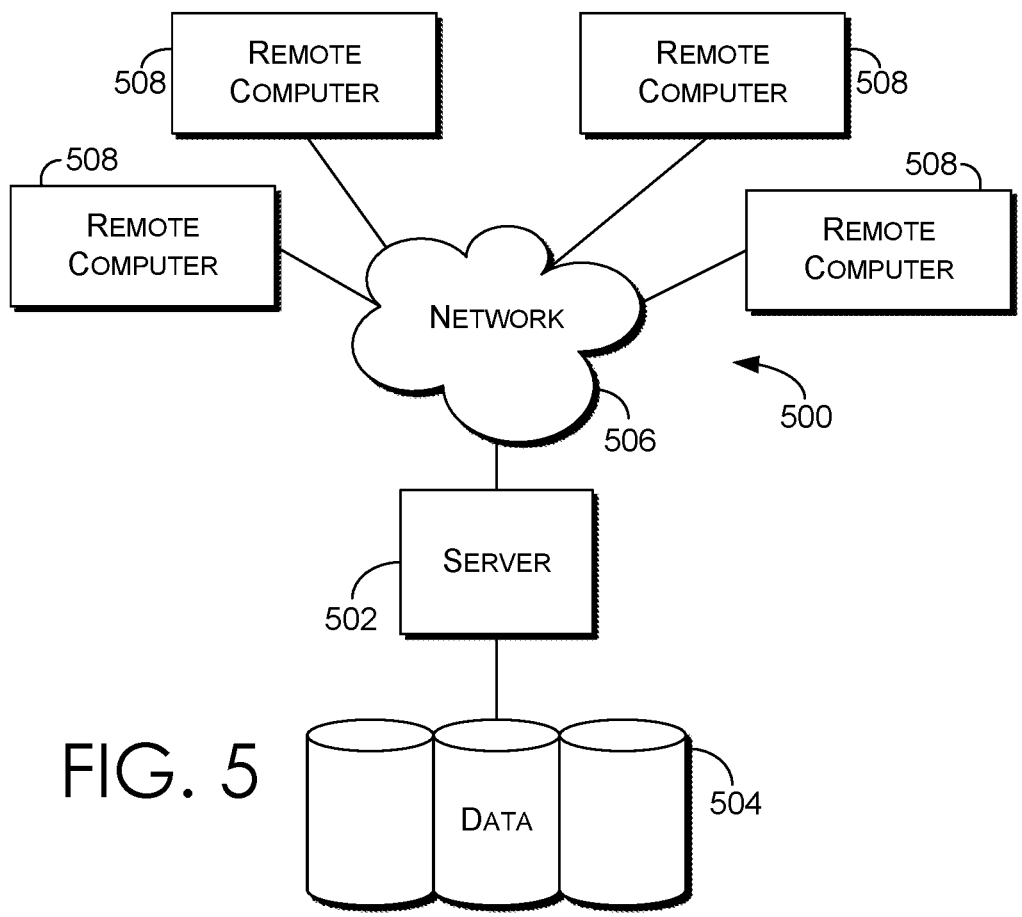
FIG. 5 depicts a block diagram of an exemplary computing environment suitable to implement embodiments of the present invention.

Turning to FIG. 5, it depicts a block diagram of an exemplary environment suitable to implement embodiments of the present invention. The exemplary computing environment 500 is suitable to implement embodiments of the present invention. It will be understood by those of ordinary skill in the art that the exemplary computing environment 500 is just one example of a suitable computing environment and is not intended to limit the scope of use or functionality of the present invention. Similarly, the exemplary computing environment 500 should not be interpreted as imputing any dependency and/or any requirements with regard to each component and combination(s) of components illustrated in FIG. 5. It will be appreciated by those having ordinary skill in the art that the connections illustrated in FIG. 5 are also exemplary as other methods, hardware, software, and devices for establishing a communications link between the components, devices, systems, and entities, as shown in FIG. 5, may be utilized in implementation of the present invention. Although the connections are depicted using one or more solid lines, it will be understood by those having ordinary skill in the art that the exemplary connections of FIG. 5 may be hardwired or wireless, and may use intermediary components that have been omitted or not included in FIG. 5 for simplicity's sake. As such, the absence of components from FIG. 5 should be not be interpreted as limiting the present invention to exclude additional components and combination(s) of components. Moreover, though devices and components are represented in FIG. 5 as singular devices and components, it will be appreciated that some embodiments may include a plurality of the devices and components such that FIG. 5 should not be considered as limiting the number of a devices or components.

Continuing, the exemplary computing environment 500 of FIG. 5 is illustrated as being a distributed environment where components and devices may be remote from one another and may perform separate tasks. The components and devices may communicate with one another and may be linked to each other using a network 506. The network 506 may include wireless and/or physical (e.g., hardwired) connections. Exemplary networks include a telecommunications network of a service provider or carrier, Wide Area Network (WAN), a Local Area Network (LAN), a Wireless Local Area Network (WLAN), a cellular telecommunications network, a Wi-Fi network, a short range wireless network, a Wireless Metropolitan Area Network (WMAN), a Bluetooth® capable network, a fiber optic network, or a combination thereof. The network 506, generally, provides the components and devices access to the Internet and web-based applications. The exemplary environment may also be a cloud computing environment.

The exemplary computing environment 500 comprises a computing device in the form of a server 502. Although illustrated as one component in FIG. 5, the present invention may utilize a plurality of local servers and/or remote servers in the exemplary computing environment 900. The server 502 may include components such as a processing unit, internal system memory, and a suitable system bus for coupling to various components, including a database or database cluster. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

The server 502 may include or may have access to computer-readable media. Computer-readable media can be any available media that may be accessed by server 502, and includes volatile and nonvolatile media, as well as removable and non-removable media. By way of example, and not limitation, computer-readable media may include computer storage media and communication media. Computer storage media may include, without limitation, volatile and nonvolatile media, as well as removable and non-removable media, implemented in any method or technology for storage of information, such as computer-readable instructions, data structures, program modules, or other data. In this regard, computer storage media may include, but is not limited to, Random Access Memory (RAM), Read-Only Memory (ROM), Electrically Erasable Programmable Read-Only Memory (EEPROM), flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 902. Computer storage media does not comprise signals per se.

Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, radio frequency (RF), infrared, and other wireless media. Combinations of any of the above also may be included within the scope of computer-readable media.

In embodiments, the server 502 uses logical connections to communicate with one or more remote computers 508 within the exemplary computing environment 500. In one embodiment, the one or more remote computers 508 comprise external computer systems that leverage object-oriented programming. In embodiments where the network 506 includes a wireless network, the server 502 may employ a modem to establish communications with the Internet, the server 502 may connect to the Internet using Wi-Fi or wireless access points, or the server 502 may use a wireless network adapter to access the Internet. The server 502 engages in two-way communication with any or all of the components and devices illustrated in FIG. 5, using the network 506. Accordingly, the server 502 may send data to and receive data from the remote computers 508 over the network 506.

Although illustrated as a single device, the remote computers 508 may include multiple computing devices. In an embodiment having a distributed network, the remote computers 508 may be located at one or more different geographic locations. In an embodiment where the remote computers 508 are a plurality of computing devices, each of the plurality of computing devices may be located across various locations such as buildings in a campus, medical and research facilities at a medical complex, offices or "branches" of a banking/credit entity, or may be mobile devices that are wearable or carried by personnel, or attached to vehicles or trackable items in a warehouse, for example.

In some embodiments, the remote computers 508 are physically located in a medical setting such as, for example, a laboratory, inpatient room, an outpatient room, a hospital, a medical vehicle, a veterinary environment, an ambulatory setting, a medical billing office, a financial or administrative office, hospital administration setting, an in-home medical care environment, and/or medical professionals' offices. By way of example, a medical professional may include physicians; medical specialists such as surgeons, radiologists, cardiologists, and oncologists; emergency medical technicians; physicians' assistants; nurse practitioners; nurses; nurses' aides; pharmacists; dieticians; microbiologists; laboratory experts; genetic counselors; researchers; students; and the like. In other embodiments, the remote computers 508 may be physically located in a non-medical setting, such as a packing and shipping facility or deployed within a fleet of delivery or courier vehicles. Remote computers 508 can also be hosted on a private or public cloud.

Continuing, the exemplary computing environment 500 includes a database 504. In some embodiments, the database 504 and at least the server 502, together, form a relational database management system. Although shown as a single component, the database 504 may be implemented using multiple data stores that are communicatively coupled to one another, independent of the geographic or physical location of a memory device. Exemplary data stores may also store data in the form of electronic records, for example, electronic medical records of patients, transaction records, billing records, task and workflow records, chronological event records, and the like. Database 504 can also be hosted on a private or public cloud.

Generally, the database 504 includes physical memory that is configured to store information encoded in data. For example, the database 504 may provide storage for computer-readable instructions, computer-executable instructions, data structures, data arrays, computer programs, applications, and other data that supports the functions and action to be undertaken using the exemplary computing environment 500 and components shown in exemplary FIG. 5.

In a computing environment having distributed components that are communicatively coupled via the network 506, program modules may be located in local and/or remote computer storage media including, for example only, memory storage devices. Embodiments of the present invention may be described in the context of computer-executable instructions, such as program modules, being executed by a computing device. Program modules may include, but are not limited to, routines, programs, objects, components, and data structures that perform particular tasks or implement particular data types. In embodiments, the server 502 may access, retrieve, communicate, receive, and update information stored in the database 504, including program modules. Accordingly, the server 502 may execute, using a processor, computer instructions stored in the database 504 in order to perform embodiments described herein.

Although internal components of the devices in FIG. 5, such as the server 502, are not illustrated, those of ordinary skill in the art will appreciate that internal components and their interconnection are present in the devices of FIG. 5.

Accordingly, additional details concerning the internal construction of the device are not further disclosed herein.

The present invention has been described in relation to particular embodiments, which are intended in all respects to be illustrative rather than restrictive. Further, the present invention is not limited to these embodiments, but variations and modifications may be made without departing from the scope of the present invention.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations.

What is claimed is:

1. One or more non-transitory media having instructions that, when executed by one or more processors associated with a Consolidated Document Architecture (CDA) assembler external to and coupled via a network to a Fast Healthcare Interoperability Resources (FHIR)-enabled system, cause the one or more processors to facilitate a plurality of operations, the operations comprising:
   identifying, by a listener component of the CDA assembler, a triggering event;
   in response to the identifying, initiating creation of a CDA document, at least by:
      presenting a script builder user interface via the CDA assembler; and
      receiving via the script builder user interface a request for generation of the CDA document;
   generating, by a script builder tool of the CDA assembler using a template script, an executable script that includes:
      script instructions indicating data to include in the CDA document, the data associated with a FHIR resource and with the FHIR-enabled system; and
      script data indicating at least one mapping of the FHIR resource to a CDA resource to include in the CDA document; and
   executing the executable script, by a runtime component of the CDA assembler, to perform:
      (a) initiating a FHIR Application Programming Interface (API) call to the FHIR-enabled system to locate the data within the FHIR-enabled system based on one or both of the script instructions and the script data, wherein initiating the FHIR API call causes querying of the FHIR-enabled system for the data and locating the data within the FHIR-enabled system responsive to the querying;
      (b) applying the at least one mapping, to the data received responsive to the querying, based on one or both of the script instructions and the script data and in response to the locating of the data;
      (c) compiling the data based on the applying; and
      (d) creating the CDA document based on the compiling, wherein the CDA document is created in a CDA format.

2. The one or more non-transitory media of claim 1, wherein the executable script comprises a user-defined script.

3. The one or more non-transitory media of claim 1, wherein the operations further comprise transmitting by the CDA assembler the CDA document to a destination disparate from the FHIR-enabled system, and wherein the destination is a system disparate from the CDA assembler and is specified by the executable script.

4. The one or more non-transitory media of claim 1, wherein the operations further comprise transmitting by the CDA assembler the CDA document to a source destination via a communication protocol component.

5. The one or more non-transitory media of claim 4, wherein the CDA document is transmitted by the CDA assembler to the communication protocol component in CDA format.

6. The one or more non-transitory media of claim 5, wherein the operations further comprise transmitting in CDA format, by the communication protocol component, the CDA document to the source destination.

7. The one or more non-transitory media of claim 6, wherein the source destination is a system disparate from the CDA assembler and from the FHIR-enabled system.

8. The one or more non-transitory media of claim 1, wherein the script data indicates a source destination, disparate from the CDA assembler and from the FHIR-enabled system, for delivery of the CDA document.

9. The one or more non-transitory media of claim 8, wherein executing the executable script by the CDA assembler causes transmission, from the CDA assembler to the source destination, of the CDA document.

10. The one or more non-transitory media of claim 1, wherein the operations further comprise transmitting the CDA document, from the CDA assembler, to a communication protocol component configured to interact with the CDA assembler and with a designated source destination.

11. The one or more non-transitory media of claim 10, wherein the communication protocol component is further configured to receive the CDA document from the CDA assembler and to transmit the CDA document to the source destination.

12. The one or more non-transitory media of claim 10, wherein the communication protocol component includes a processor.

13. The one or more non-transitory media of claim 1, wherein the operations further comprise:
   detecting, at the CDA assembler, a prescribed time; and
   initiating, by the runtime component of the CDA assembler, execution of the executable script in response to detecting the prescribed time.

14. The one or more non-transitory media of claim 13, wherein the prescribed time is set, at the CDA assembler, based on a time of an encounter of a patient with a clinician.

15. The one or more non-transitory media of claim 13, wherein:
   the listener component is configured to:
      identify the prescribed time; and
      provide a notification of the identified prescribed time to the runtime component of the CDA assembler, and
   the runtime component is configured to detect the prescribed time based on the notification.

16. The one or more non-transitory media of claim 13, wherein the prescribed time indicates a preset time of day that is specified in units of time, corresponding to hours and minutes, and stored prior to the detection by the listener component of the prescribed time.

17. The one or more non-transitory media of claim 13, wherein the listener component is configured to monitor a clock to detect the prescribed time.

18. The one or more non-transitory media of claim 13, wherein the CDA assembler is distinct from a medical facility that includes the FHIR-enabled system.

19. The one or more non-transitory media of claim 1, wherein the operations further comprise:

identifying, by an addresser component of the CDA assembler and after the executing, a destination device disparate from the FHIR-enabled system and from the CDA assembler;

addressing, by the addresser component and after the executing, the CDA document for transmission to a communication protocol component; and communicating, by the addresser component and after the executing, the CDA document to the communication protocol component for delivery by the communication protocol component to the destination device.

20. The one or more non-transitory media of claim 19, wherein the addresser component is configured to identify the destination device based on a determination, by the addresser component and based on the executing, of an association between the CDA document and the destination device.

21. The one or more non-transitory media of claim 20, wherein the addresser component is further configured to work with the communication protocol component after the executing to transmit the CDA document from the FHIR-enabled system to the destination device.

22. A method, comprising:

identifying, by a listener component of a Consolidated Document Architecture (CDA) assembler external to and coupled via a network to a Fast Healthcare Interoperability Resources (FHIR)-enabled system, a triggering event;

in response to the identifying, initiating creation of a CDA document, at least by:

presenting a script builder user interface via the CDA assembler; and receiving via the script builder user interface a request for generation of the CDA document;

generating an executable script via a script builder tool of the CDA assembler using a template script, wherein the executable script includes:

script instructions indicating data to include in the CDA document, the data associated with a FHIR resource and with the FHIR-enabled system; and script data indicating at least one mapping of the FHIR resource to a CDA resource to include in the CDA document; and executing the executable script, by a runtime component of the CDA assembler, to perform:

(a) initiating a FHIR Application Programming Interface (API) call to the FHIR-enabled system to locate the data within the FHIR-enabled system based on one or both of the script instructions and the script data, wherein initiating the FHIR API call causes querying of the FHIR-enabled system for the data and locating the data within the FHIR-enabled system responsive to the querying;

(b) applying the at least one mapping, to the data received responsive to the querying, based on one or both of the script instructions and the script data and in response to the locating of the data;

(c) compiling the data based on the applying; and (d) creating the CDA document based on the compiling, wherein the CDA document is created in a CDA format.

23. The method of claim 22, further comprising:

designating a destination, for the CDA document, that is disparate from the FHIR-enabled system; and communicating the CDA document to the destination utilizing a messaging protocol.

24. A system having one or more processors configured to facilitate a plurality of operations, the operations comprising:

identifying, by a listener component of a Consolidated Document Architecture (CDA) assembler external to and coupled via a network to a Fast Healthcare Interoperability Resources (FHIR)-enabled system, a triggering event;

in response to the identifying, initiating creation of a CDA document, at least by:

presenting a script builder user interface via the CDA assembler; and receiving via the script builder user interface a request for generation of the CDA document;

generating an executable script via a script builder tool of the CDA assembler using a template script, wherein the executable script includes:

script instructions indicating data to include in the CDA document, the data associated with a FHIR resource and with the FHIR-enabled system; and script data indicating at least one mapping of the FHIR resource to a CDA resource to include in the CDA document; and executing the executable script, by a runtime component of the CDA assembler, to perform:

(a) initiating a FHIR Application Programming Interface (API) call to the FHIR-enabled system to locate the data within the FHIR-enabled system based on one or both of the script instructions and the script data, wherein initiating the FHIR API call causes querying of the FHIR-enabled system for the data and locating the data within the FHIR-enabled system responsive to the querying;

(b) applying the at least one mapping, to the data received responsive to the querying, based on one or both of the script instructions and the script data and in response to the locating of the data;

(c) compiling the data based on the applying; and (d) creating the CDA document based on the compiling, wherein the CDA document is created in a CDA format.

25. The system of claim 24, wherein the executable script comprises at least one of a user-defined script or a template script.

26. The system of claim 24, wherein the one or more processors are further configured to:

designate an electronic health record system disparate from the FHIR-enabled system; and communicate the CDA document to the electronic health record system utilizing a messaging protocol.

* * * * *